US006664384B1

(12) United States Patent
Xu et al.

(10) Patent No.: US 6,664,384 B1
(45) Date of Patent: Dec. 16, 2003

(54) DUPLICATED CASSAVA VEIN MOSAIC VIRUS ENHANCERS AND USES THEREOF

(75) Inventors: Dongmei Xu, Lexington, KY (US); Mark T. Nielsen, Lexington, KY (US)

(73) Assignee: Profigen, Inc., Nashville, TN (US)

( * ) Notice: Subject to any disclaimer, the term of this patent is extended or adjusted under 35 U.S.C. 154(b) by 23 days.

(21) Appl. No.: 09/641,466

(22) Filed: Aug. 18, 2000

Related U.S. Application Data

(60) Provisional application No. 60/149,763, filed on Aug. 19, 1999.

(51) Int. Cl.[7] ........................ C07H 21/04; C12N 15/00; C12N 5/00; C12N 15/82; A01H 11/00

(52) U.S. Cl. .................. 536/23.1; 435/320.1; 435/410; 435/468; 800/295

(58) Field of Search .............................. 435/320.1, 410, 435/419, 468; 536/23.1; 800/295

(56) References Cited

U.S. PATENT DOCUMENTS 5,164,316 A * 11/1992 McPherson et al. ..... 435/240.4

FOREIGN PATENT DOCUMENTS

| | | |
|---|---|---|
| WO | WO 97/47756 | 12/1997 |
| WO | WO 97/48819 | * 12/1997 |

OTHER PUBLICATIONS

L. Comai et al., "Novel and Useful Properties of a Chimeric Plant Promoter Combining CaMV 35S and MAS Elements", Plant Mol. Biol. 15:373–81 (1990).

V. Sundaresan et al., "Patterns of Gene Action in Plant Development Revealed by Enhancer Trap and Gene Trap Transposable Elements", Genes Dev. 9:1797–810 (1995).

Kay et al., "Duplication of CaMV 35S Promoter Sequences Creates a Strong Enhancer for Plant Genes," *Science* 236:1299–1302 (1987).

Verdaguer et al., "Functional analysis of the cassava vein mosaic virus promoter and its usage for cassava genetic engineering," *Trop. Agric.* 75:317–319 (1998).

Verdaguer et al., "Functional organization of the cassava vein mosaic virus (CsVMV) promoter," *Plant Molecular Biology* 37:1055–1067 (1998).

* cited by examiner

*Primary Examiner*—Jeffrey Fredman
*Assistant Examiner*—Prabha Chunduru
(74) *Attorney, Agent, or Firm*—Clark & Elbing LLP

(57) ABSTRACT

The invention features duplicated enhancer domains and enhancer cassettes. The invention also features expression constructs having one or more duplicated enhancer domains and a promoter under the regulation of the duplicated enhancer domains. The expression construct is useful for increasing the expression of any nucleic acid molecule that is operably linked to the expression construct. Accordingly, the invention also features a method for expressing a nucleic acid molecule through the use of an expression construct of the present invention.

32 Claims, 9 Drawing Sheets

SEQ ID NO: 1

CCAGAAGGTA ATTATCCAAG ATGTAGCATC AAGAATCCAA TGTTTACGGG AAAAACTATG

GAAGTATTAT GTGAGCTCAG CAAGAAGCAG ATCAATATGC GGCACATATG CAACCTATGT

TCAAAAATGA AGAATGTACA GATACAAGAT CCTATACTGC CAGAATACGA AGAAGAATAC

GTAGAAATTG AAAAAGAAGA ACCAGGCGAA GAAAAGAATC TTGAAGACGT AAGCACTGAC

GACAACAATG AAAAGAAGAA GATAAGGTCG GTGATTGTGA AAGAGACATA GAGGACACAT

GTAAGGTGGA AAATGTAAGG GCGGAAAGTA ACCTTATCAC AAAGGAATCT TATCCCCCAC

TACTTATCCT TTTATATTTT TCCGTGTCAT TTTTGCCCTT GAGTTTTCCT ATATAAGGAA

+1

CCAAGTTCGG CATTTGTGAA AACAAGAAAA AATTTGGTGT AAGCTATTTT CTTTGAAGTA

CTGAGGATAC AAGTTCAGAG AAATTTGTAA GTTTG

Fig. 1

CV-2 (SEQ ID NO: 2)

CCAGAAGGTA ATTATCCAAG ATGTAGCATC AAGAATCCAA TGTTTACGGG AAAAACTATG
GAAGTATTAT GTGAGCTCAG CAAGAAGCAG ATCAATATGC GGCACATATG CAACCTATGT
TCAAAAATGA AGAATGTACA GATACAAGAT CCTATACTGC CAGAATACGA AGAAGAATAC
GTAGAAATTG AAAAAGAAGA ACCAGGCGAA GAAAAGAATC TTGAAGACGT AAGCACTGAC
GACAACAATG AAAAGAAGAA GATAAGGTCG GTGATTGTGA AAGAGACATA GAGGACACAT
GTAAGGTGGA AAATGTAAGG GCGGAAAGTA ACAAGCTTCC AGAAGGTAAT TATCCAAGAT
GTAGCATCAA GAATCCAATG TTTACGGGAA AAACTATGGA AGTATTATGT GAGCTCAGCA
AGAAGCAGAT CAATATGCGG CACATATGCA ACCTATGTTC AAAAATGAAG AATGTACAGA
TACAAGATCC TATACTGCCA GAATACGAAG AAGAATACGT AGAAATTGAA AAAGAAGAAC
CAGGCGAAGA AAAGAATCTT GAAGACGTAA GCACTGACGA CAACAATGAA AAGAAGAAGA
TAAGGTCGGT GATTGTGAAA GAGACATAGA GGACACATGT AAGGTGGAAA ATGTAAGGGC
GGAAAGTAAC CTTATCACAA AGGAATCTTA TCCCCCACTA CTTATCCTTT TATATTTTTC
CGTGTCATTT TTGCCCTTGA GTTTTCCTAT ATAAGGAACC AAGTTCGGCA TTTGTGAAAA
CAAGAAAAAA TTTGGTGTAA GCTATTTTCT TTGAAGTACT GAGGATACAA GTTCAGAGAA
ATTTGTAAGT TTG

Fig. 4A

CV-3 (SEQ ID NO: 3)

CCAGAAGGTA ATTATCCAAG ATGTAGCATC AAGAATCCAA TGTTTACGGG AAAAACTATG
GAAGTATTAT GTGAGCTCAG CAAGAAGCAG ATCAATATGC GGCACATATG CAACCTATGT
TCAAAAATGA AGAATGTACA GATACAAGAT CCTATACTGC CAGAATACGA AGAAGAATAC
GTAGAAATTG AAAAAGAAGA ACCAGGCGAA GAAAAGAATC TTGAAGACGT AAGCACTGAC
GACAACAATG AAAAGAAGAA GATAAGGTCG GTGATTGTGA AAGAGACATA GAGGACACAT
GTAAGGTGGA AAATGTAAGG GCGGAAAGTA ACAAGCTTGA TAAGGTCGGT GATTGTGAAA
GAGACATAGA GGACACATGT AAGGTGGAAA ATGTAAGGGC GGAAAGTAAC CTTATCACAA
AGGAATCTTA TCCCCCACTA CTTATCCTTT TATATTTTTC CGTGTCATTT TTGCCCTTGA
GTTTTCCTAT ATAAGGAACC AAGTTCGGCA TTTGTGAAAA CAAGAAAAAA TTTGGTGTAA
GCTATTTTCT TTGAAGTACT GAGGATACAA CTTCAGAGAA ATTTGTAAGT TTG

Fig. 4B

CV-4 (SEQ ID NO: 4)

CCAGAAGGTA ATTATCCAAG ATGTAGCATC AAGAATCCAA TGTTTACGGG AAAAACTATG
GAAGTATTAT GTGAGCTCAG CAAGAAGCAG ATCAATATGC GGCACATATG CAACCTATGT
TCAAAAATGA AGAATGTACA GATACAAGAT CCTATACTGC CAGAATACGA AGAAGAATAC
GTAGAAATTG AAAAAGAAGA ACCAGGCGAA GAAAAGAATC TTGAAGACGT AAGCACTGAC
GACAACAATG AAAAGAAGAA GCTTCCAGAA GGTAATTATC CAAGATGTAG CATCAAGAAT
CCAATGTTTA CGGGAAAAAC TATGGAAGTA TTATGTGAGC TCAGCAAGAA GCAGATCAAT
ATGCGGCACA TATGCAACCT ATGTTCAAAA ATGAAGAATG TACAGATACA AGATCCTATA
CTGCCAGAAT ACGAAGAAGA ATACGTAGAA ATTGAAAAAG AAGAACCAGG CGAAGAAAAG
AATCTTGAAG ACGTAAGCAC TGACGACAAC AATGAAAAGA AGAAGATAAG GTCGGTGATT
GTGAAAGAGA CATAGAGGAC ACATGTAAGG TGGAAAATGT AAGGGCGGAA AGTAACAAGC
TTGATAAGGT CGGTGATTGT GAAAGAGACA TAGAGGACAC ATGTAAGGTG GAAAATGTAA
GGGCGGAAAG TAACCTTATC ACAAAGGAAT CTTATCCCCC ACTACTTATC CTTTTATATT
TTTCCGTGTC ATTTTTGCCC TTGAGTTTTC CTATATAAGG AACCAAGTTC GGCATTTGTG
AAAACAAGAA AAAATTTGGT GTAAGCTATT TTCTTTGAAG TACTGAGGAT ACAACTTCAG
AGAAATTTGT AAGTTTG

Fig. 4C

CV-5 (SEQ ID NO: 5)

CCAGAAGGTA ATTATCCAAG ATGTAGCATC AAGAATCCAA TGTTTACGGG AAAAACTATG
GAAGTATTAT GTGAGCTCAG CAAGAAGCAG ATCAATATGC GGCACATATG CAACCTATGT
TCAAAAATGA AGAATGTACA GATACAAGAT CCTATACTGC CAGAATACGA AGAAGAATAC
GTAGAAATTG AAAAAGAAGA ACCAGGCGAA GAAAAGAATC TTGAAGACGT AAGCACTGAC
GACAACAATG AAAAGAAGAA GATAAGGTCG GTGATTGTGA AAGAGACATA GAGGACACAT
GTAAGGTGGA AAATGTAAGG GCGGAAAGTA ACAAGCTTCC AGAAGGTAAT TATCCAAGAT
GTAGCATCAA GAATCCAATG TTTACGGGAA AAACTATGGA AGTATTATGT GAGCTCAGCA
AGAAGCAGAT CAATATGCGG CACATATGCA ACCTATGTTC AAAAATGAAG AATGTACAGA
TACAAGATCC TATACTGCCA GAATACGAAG AAGAATACGT AGAAATTGAA AAAGAAGAAC
CAGGCGAAGA AAAGAATCTT GAAGACGTAA GCACTGACGA CAACAATGAA AAGAAGAAGA
TAAGGTCGGT GATTGTGAAA GAGACATAGA GGACACATGT AAGGTGGAAA ATGTAAGGGC
GGAAAGTAAC AAGCTTGATA AGGTCGGTGA TTGTGAAAGA GACATAGAGG ACACATGTAA
GGTGGAAAAT GTAAGGGCGG AAAGTAACCT TATCACAAAG GAATCTTATC CCCCACTACT
TATCCTTTTA TATTTTTCCG TGTCATTTTT GCCCTTGAGT TTTCCTATAT AAGGAACCAA
GTTCGGCATT TGTGAAAACA AGAAAAAATT TGGTGTAAGC TATTTTCTTT GAAGTACTGA
GGATACAACT TCAGAGAAAT TTGTAAGTTT G

Fig. 4D

CV-6 (SEQ ID NO: 6)

CCAGAAGGTA ATTATCCAAG ATGTAGCATC AAGAATCCAA TGTTTACGGG AAAAACTATG
GAAGTATTAT GTGAGCTCAG CAAGAAGCAG ATCAATATGC GGCACATATG CAACCTATGT
TCAAAAATGA AGAATGTACA GATACAAGAT CCTATACTGC CAGAATACGA AGAAGAATAC
GTAGAAATTG AAAAAGAAGA ACCAGGCGAA GAAAAGAATC TTGAAGACGT AAGCACTGAC
GACAACAATG AAAAGAAGAA GATAAGGTCG GTGATTGTGA AAGAGACATA GAGGACACAT
GTAAGGTGGA AAATGTAAGG GCGGAAAGTA ACAAGCTTGT TACTTTCCGC CCTTACATTT
TCCACCTTAC ATGTGTCCTC TATGTCTCTT TCACAATCAC CGACCTTATC TTCTTCTTTT
CATTGTTGTC GTCACTGCTT ACGTCTTCAA GATTCTTTTC TTCGCCTGGT TCTTCTTTTT
CAATTTCTAC GTATTCTTCT TCGTATTCTG GCAGTATAGG ATCTTGTATC TGTACATTCT
TCATTTTTGA ACATAGGTTG CATATGTGCC GCATATTGAT CTGCTTCTTG CTGAGCTCAC
ATAATACTTC CATAGTTTTT CCCGTAAACA TTGGATTCTT GATGCTACAT CTTGGATAAT
TACCTTCTGG AAGCTTGATA AGGTCGGTGA TTGTGAAAGA GACATAGAGG ACACATGTAA
GGTGGAAAAT GTAAGGGCGG AAAGTAACCT TATCACAAAG GAATCTTATC CCCCACTACT
TATCCTTTTA TATTTTTCCG TGTCATTTTT GCCCTTGAGT TTTCCTATAT AAGGAACCAA
GTTCGGCATT TGTGAAAACA AGAAAAAATT TGGTGTAAGC TATTTTCTTT GAAGTACTGA
GGATACAACT TCAGAGAAAT TTGTAAGTTT G

Fig. 4E

DUPLICATED CASSAVA VEIN MOSAIC VIRUS ENHANCERS AND USES THEREOF

CROSS-REFERENCE TO RELATED APPLICATIONS

This application claims benefit of U.S. Provisional Application No. 60/149,763 (filed Aug. 19, 1999), now pending, which is hereby incorporated by reference.

BACKGROUND OF THE INVENTION

The invention relates to methods of manipulating gene expression in plants.

The ability to manipulate gene expression provides a means of producing new characteristics in transformed plants. There are many situations in which high or increased levels of gene expression may be desired. For example, it is desirable to increase production of a protein that itself maximizes the disease resistance, yield, flavor, or any other commercially important attribute of a plant. Similarly, the regulation of endogenous gene expression by the exogenous expression of antisense, ribozyme RNA, or transgene silencing may result in more valuable plants or plant products. The enhancement of expression, through the use of the invention disclosed herein, would facilitate these possibilities.

SUMMARY OF THE INVENTION

We have discovered duplicated enhancer domains for use in the enhancement of gene expression in transgenic plants. The duplicated enhancer domains have a plurality of the repetitive units of one or more enhancers derived from cassava vein mosaic virus (CsVMV). The duplicated enhancer domains are preferably accompanied by a promoter that includes an RNA polymerase binding site and an mRNA initiation site. Expression constructs, including a duplicated enhancer domain and a promoter, provide for enhanced expression of a desired trait compared to that achieved with the promoter in the absence of the duplicated enhancer domain.

Accordingly, in a first aspect, the invention features an enhancer cassette that includes a duplicated enhancer domain derived from a cassava vein mosaic virus.

Preferably, the enhancer cassette includes a component having the formula $(X\text{-}Y)^n$, wherein X corresponds to the enhancer domain derived from a cassava vein mosaic virus, Y is an intervening spacer domain having a sequence that is placed between enhancer domains and is typically between about zero and about five hundred nucleotides inclusive (preferably between zero and about one hundred nucleotides and, more preferably, between zero and thirty nucleotides), and n is an integer between 2 and 8 inclusive. In preferred embodiments, the enhancer domain (X) has a sequence that includes nucleotides 1 to about 261 of SEQ ID NO: 1, nucleotides 1 to about 332 of SEQ ID NO: 1, or nucleotides of about 262 to about 332 of SEQ ID NO: 1. Preferably, in the formula of the first aspect, $(X\text{-}Y)^n$, n is 2. The spacer domains (Y) can be identical or different. For example, an enhancer cassette having the formula $(X\text{-}Y)^3$ can have three different spacer sequences.

In a related aspect, the invention features an expression construct including the enhancer cassette of the first aspect and a second component that includes a promoter having an RNA polymerase binding site and an mRNA initiation site. A preferred promoter is a cassava vein mosaic virus promoter, such as one included in the nucleotides from about 333 to about 444 of SEQ ID NO: 1. The promoter can also be a heterologous promoter (for example, a Ti-plasmid promoter such as the T-DNA gene 5 or 7 promoter). In preferred embodiments, the expression construct includes a sequence corresponding to SEQ ID NO: 2. (FIG. 4A), SEQ ID NO: 3 (FIG. 4B), SEQ ID NO: 4 (FIG. 4C), SEQ ID, NO: 5 (FIG. 4D), or SEQ ID NO: 6 (FIG. 4E).

The expression construct may further include, as a third component, a nucleic acid molecule of interest, wherein the first, second, and third components are operably linked so that the nucleic acid molecule is transcribed. The third component of the construct can encode a protein providing disease or insect resistance, an antisense RNA, a selectable marker (e.g., GUS, GFP, and the like), a non-translatable RNA molecule, or any protein or RNA that improves or results in a desired attribute.

This three-component expression construct of the present invention, when placed in a transcription medium capable of supporting transcription, typically results in increased transcription of the nucleic acid molecule relative to transcription of the nucleic acid molecule operably linked to an expression construct that has only one CsVMV enhancer domain.

In related aspects, the invention also features vectors and cells that include the enhancer cassette of the first aspect. Preferably, the cell is a eukaryotic cell, and, more preferably, a plant cell (e.g., from a monocotylenous plant or a dicotylenous plant).

In another related aspect, the invention also features a transgenic plant that includes the enhancer cassette of the first aspect.

In yet another related aspect, the invention features a method for expressing a nucleic acid molecule. The method includes transforming a cell (for example, a plant cell) with an expression construct that includes (a) a first component having the formula $(X\text{-}Y)^n$, wherein X corresponds to the enhancer domain derived from a cassava vein mosaic virus, Y is an intervening spacer domain having a sequence that is placed between enhancer domains and is typically between about zero and about five hundred nucleotides inclusive (preferably between zero and about one hundred nucleotides and, more preferably, between zero and thirty nucleotides), and n is an integer between 2 and 8 inclusive; (b) a second component that includes a promoter (e.g., an RNA polymerase binding, site and an mRNA initiation site); and (c) a third component that includes the nucleic acid molecule to be expressed, wherein the first, second, and third components are operably linked so that the nucleic acid molecule is transcribed. In preferred embodiments, the enhancer domain (X) consists of a sequence that includes nucleotides from about 1 to about 261 of SEQ ID NO: 1, nucleotides from about 1 to about 332 of SEQ ID NO: 1, and nucleotides from about 262 to about 332 of SEQ ID NO: 1. Preferably, in the formula of the third aspect, $(X\text{-}Y)^n$, n is 2.

The promoter can be any promoter that is functional in the transformed cell, but preferably is a cassava vein mosaic virus promoter (e.g. one included in nucleotides from about 333 to about 444 of SEQ ID NO: 1).

The third component of the expression construct can encode a protein providing disease or insect resistance, an antisense RNA, a selectable marker (e.g., GUS, GFP, and the like), or any protein or RNA including but not limited to a nontranslatable RNA or any RNA molecule capable of inducing transgene silencing.

As used herein, by "nucleic acid" is meant either DNA or RNA. A "nucleic acid molecule" may be a single-stranded or double-stranded polymer of deoxyribonucleotide or ribonucleotide bases. Unless otherwise specified, the left hand direction of the sequence of a single-stranded nucleic acid molecule is the 5' end, and the left hand direction of double-stranded nucleic molecule is referred to as the 5' direction.

By "promoter" is meant a region of nucleic acid, upstream from a translational start codon, which is involved in recognition and binding of RNA polymerase and other proteins to initiate transcription. A "plant promoter" is a promoter capable of initiating transcription in a plant cell, and may or may not be derived from a plant cell. A "CsVMV promoter" is one derived from the promoter region of a CsVMV genome and that, when operably linked to a heterologous. nucleic acid molecule, is capable of initiating transcription of that molecule when present in a transcription medium capable of supporting transcription, such as in a plant cell, a plant, or in vitro.

Exemplary transcription media include, for example, a plant cell, plant protoplasts, or other plant tissue culture configurations, non-differentiated plant cells, differentiated plant cells (such as cultured plantlets), transgeinic plants, and mature plants. Also included are in vitro expression systems such as reconstituted expression medium composed of components required to support transcription, as are known in the art.

By "enhancer domain" is meant a nucleic acid sequence that, when positioned proximate to a promoter and present in a transcription medium capable of supporting transcription, confers increased expression relative to the expression resulting from the promoter in,the absence of the enhancer domain. By "enhancer cassette" is meant a nucleic acid sequence that includes an enhancer domain and, optionally, additional sequence that does not enhance expression (e.g; intervening spacer domain).

By "duplicated enhancer domain" is meant two or more copies of an enhancer domain. Preferably, the number of copies is between about two and about four. The enhancer domains can be in the same or opposite orientation, and can be contiguous or noncontiguous. In the case of expression constructs having two duplicated enhancer domains (e.g., domain A and domain B), the orientation and the 5' to 3' order (e.g., 5'-AABB-3' vs. 5'-ABAB-3') are not limitations to the invention. The enhancer domains may also be separated by intervening spacer domains as described herein.

By "Operably linked" is meant that a nucleic acid molecule to be transcribed and an expression construct (i.e., a promoter and an enhancer domain) are connected in such a way as to permit transcription of the nucleic acid molecule in a suitable transcription medium.

By "derived from" is meant that the nucleic acid molecule was either made or designed from a second nucleic acid molecule, the derivative retaining the functional features thereof.

By "expression construct" is meant a nucleic acid molecule that is capable of directing transcription. An expression construct of the present invention includes, at the least, a duplicated CsVMV enhancer domain and a promoter. Additional domains, such as a transcription termination signal, may also be included, as described herein.

By "vector" or "expression vector" is meant an expression system, a nucleic acid-based shuttle vehicle, a nucleic acid molecule adapted for nucleic acid delivery, or an autonomous self-replicating circular DNA (e.g., a plasmid). When a vector is maintained in a host cell, the vector can either be stably replicated by the cells during mitosis as an autonomous structure, incorporated within the genome of the host cell, or maintained in the host cell's nucleus or cytoplasm.

By "plasmid" is meant an autonomous DNA molecule capable of replication in a cell, and includes both expression and nonexpression types.

By "heterologous" is meant that the nucleic acid molecule originates from a foreign source or, if from the same source, is modified from its original form or sequence. Thus, a "heterologous promoter" is a promoter not normally associated with the enhancer domain that is duplicated. Similarly, a heterologous nucleic acid molecule that is modified from its original form or is from a source different from the source from which the promoter to which it is operably linked was derived.

The term "plant" includes any cell having a plastid, and can include whole plants, plant organs (e.g., stems, leaves, roots, etc.), seeds, and cells. The class of plants that can be used in the method of the invention is generally as broad as the class of higher plants amenable to transformation techniques, including both monocots and dicots.

By "transgene" is meant any piece of a nucleic acid molecule (for example, DNA) which is inserted by artifice into a cell, and becomes part of the organism (integrated into the genome or maintained extrachromosomally) which develops from that cell. Such a transgene may include a gene which is partly or entirely heterologous (i.e., foreign) to the transgenic organism, or may represent a gene homologous to an endogenous gene of the organism.

By "transgenic plant" is meant a plant containing a transgene. For example, a plant cell transformed with a vector containing the expression construct of the present invention operably linked to a heterologous nucleic acid molecule can be used to produce a transgenic plant having altered phenotypic characteristics.

Other features and advantages of the invention will be apparent from the following description of the preferred embodiments thereof, and from the claims.

BRIEF DESCRIPTION OF THE DRAWINGS

FIG. 1 is a schematic illustration showing the sequence of the region immediately 5' to the CsVMV translational start site. "+1" demarcates the first nucleotide of the mRNA.

FIGS. 4A–4D are schematic illustrations showing the nucleotide sequences of expression constructs CV-2, CV-3, CV-4, and CV-5, respectively.

FIG. 4E is a schematic illustration showing the nucleotide sequence of expression construct CV-6, in which fragment CVA-5 (see FIG. 2B) is in the opposite orientation to which it is found in CV-5. In FIGS. 4A–4E, the nucleotides in bold represent nucleotides added in order to create a restriction site. One skilled in the art will recognize that these nucleotides may be omitted or replaced with other nucleotides if desired.

DETAILED DESCRIPTION OF THE INVENTION

The present invention provides novel duplicated enhancer domains and enhancer cassettes. The invention also provides expression constructs having one or more duplicated enhancer domains and a promoter under the regulation of the duplicated enhancer domains. In the expression construct, the duplicated enhancer domains increase the transcription efficiency, resulting in greater expression of any nucleic acid molecule that is operably linked to the expression construct. Of particular interest is enhanced expression of inserted gene sequences which may be of the same genetic origin as the host or of foreign origin, either the naturally occurring sequences, in either sense and antisense orientations, or synthetically prepared sequences.

Duplicated CsVMV Enhancer Domains

Figure 2A:
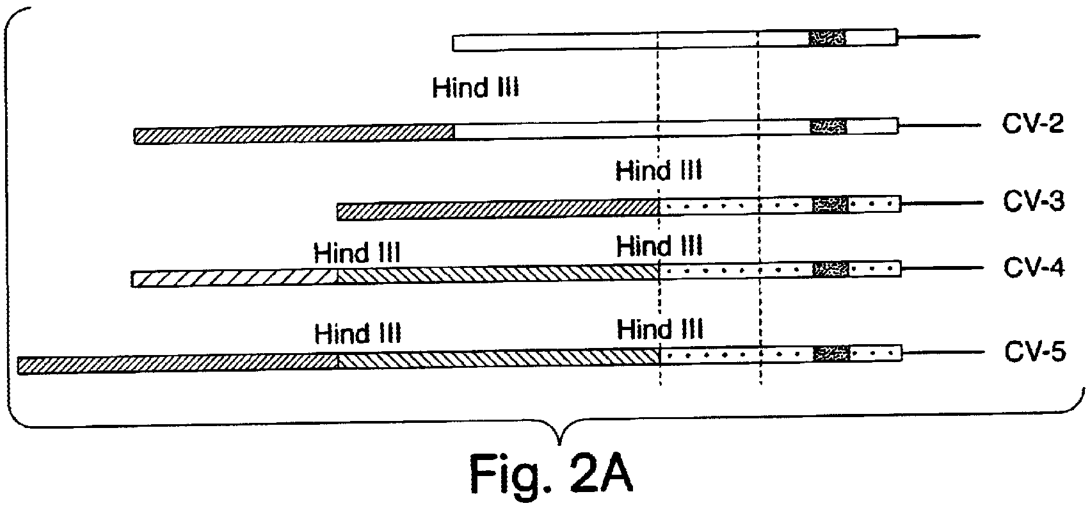
FIG. 2A is a schematic illustration showing examples of expression constructs CV-2, CV-3, CV-4, and CV-5, each of which having a duplicated enhancer domain. In each of these examples, the CsVMV promoter is used, although it is understood that this could be replaced with another promoter, as described herein. It is also understood that additional modifications, such as the addition of spacer sequences between the enhancer domains or the inversion of the orientation of one or more enhancer d6mains, would not substantially affect the transcriptional activity of the expression constructs.
Figure 2B:
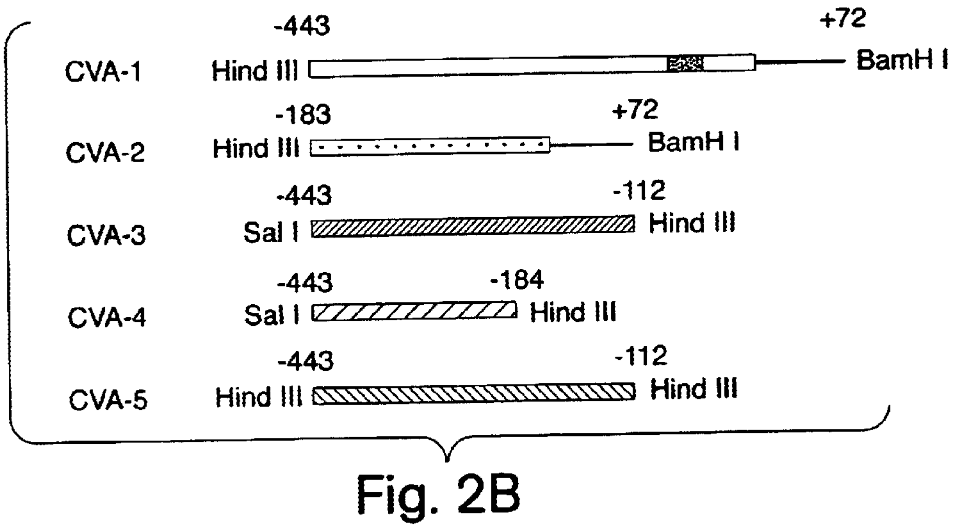
FIG. 2B is a schematic illustration showing the fragments used in the ligation strategy used to generate the expression constructs of FIG. 2A. The restriction sites have been generated during PCR of individual fragments. These restriction sites are included to exemplify the general strategy to ligate the fragments together. It will be understood that other methods known in the art, as described herein, may also be used to make the duplicated enhancer domains and expression constructs of the present invention.

In one embodiment, the invention features duplicated enhancer domains. The duplicated enhancer domains of the present invention are derived from CsVMV, a double stranded DNA plant pararetrovirus (Calvert et al., J. Gen. Virol. 76:1271, 1995), the genomic sequence of which has been previously determined (GenBank Accession Nos. U59751 and U20341), including the region containing the promoter (Verdaguer et al., Plant Mol. Biol. 31:1129, 1996; PCT publication WO 97/48819). Taking the first nucleotide of the mRNA as position +1, enhancer domains are located from about −60 to about −700 bp. Preferred enhancer domains correspond to nucleotides from about −443 to about −183, from about −443 to about −112, and from about −182 to about −112 (nucleotides for about 1 to about 261, nucleotides for about 1 to about 332, and nucleotides for about 262 to about 332 of SEQ ID NO: 1, respectively), as shown in FIGS. 2A and 2B. It will be understood that the nucleotide positions can be altered by about five to about ten nucleotides without substantially altering the expression-enhancing ability of the enhancer domain. The enhancer domain that is duplicated will usually be about 20 to about 350 bp.

Preferably, the duplicated enhancer domain is incorporated into an enhancer cassette having the formula $(X\text{-}Y)^n$, wherein X corresponds to an enhancer derived from CsVMV, Y is a sequence between about zero and about thirty nucleotides inclusive, and n is an integer between 2 and 8 inclusive. In preferred embodiments; X has a sequence that includes nucleotides 1 to about 261, nucleotides 1 to about 332, and nucleotides 262 to about 332 of SEQ ID NO: 1.

Expression Constructs

In one particular embodiment of the present invention, the duplicated enhancer domains or enhancer cassettes are placed in the proximity of a promoter; together, these form an expression construct. Exemplary expression constructs are shown in FIG. 2A and FIGS. 4A–4E.

An enhancer domain is cis-acting and desirably is located within about 5 kb, typically about 2 kb, more typically adjacent to or within about 1 kb of a promoter to be enhanced. The combination of the duplicated enhancer domain and the promoter is considered to be an "expression construct." In the expression construct, the enhancer domains may be in either orientation with respect to each other as well as to the promoter, and can be located 5' or 3' in relation to the promoter they enhance, usually in the 5' direction.

A duplicated enhancer domain of the present invention finds use with a wide variety of promoters, including promoters that are naturally found under the control of the enhancer (i.e., adjacent and homologous) and those not normally associated with the particular promoter (i.e., heterologous).

The duplicated enhancer domain and promoter may be from the same or different kingdom, family, or species. Species of interest include viruses, prokaryotes and eukaryotes, such as bacteria, plants, insects, and mammals. Combinations may include, for example, (i) enhancer domains from CsVMV combined with a promoter derived from a host for the virus; (ii) enhancer domains from CsVMV combined with a promoter from a related virus; and (iii) enhancer domains and a promoter, each of which is derived from CsVMV.

In addition to the aforementioned duplicated enhancer domain and promoter, the expression constructs may also include regulatory control regions which are generally present in the 3' regions of plant genes (Thornburg et al., Proc. Natl. Acad. Sci. U.S.A. 84:744, 1987; An et al., Plant Cell 1:115, 1989). For example, a 3' terminator region may be included in the expression vector to increase stability of the mRNA. One such terminator region may be derived from the PI-II terminator region of potato. In addition; other commonly used terminators are derived from the octopine or nopaline synthase signals.

Expression Vectors

Figure 3:
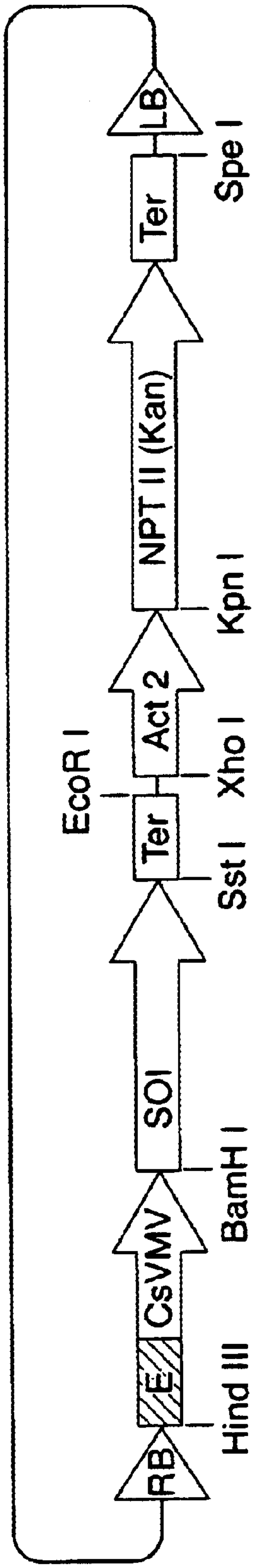
FIG. 3 is a schematic illustration showing an exemplary vector containing (i) a duplicated CsVMV enhancer domain (E) and a CsVMV promoter (CsVMV) operably linked to a nucleic acid sequence of interest (SOI), followed by a terminator (Ter); and (ii) an Act2 promoter operably linked to a gene conferring kanamycin resistance (NPT II), also followed by a terminator.

An expression vector, including an expression construct, is shown in FIG. 3. Typically, a vector containing an expression construct of the present invention also contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Genes encoding a detectable enzyme (e.g., betaglucuronidase (GUS);, see U.S. Pat. No. 5,268,463) are also useful markers. Alternatively, the green-fluorescent protein from the jellyfish *Aequorea victoria* may be used as a selectable marker (Sheen et al., Plant J. 8:777, 1995; Chiu et al., Curr. Biol. 6:325, 1996)., Finally, genes encoding herbicide resistance may be used as selectable markers; useful herbicide resistance genes include the bar gene encoding the enzyme phosphinothricin acetyltransferase and conferring resistance to the broad spectrum herbicide Basta® (Hoechst Marion Roussel, Frankfurt, Germany). Other selectable marker genes confer resistance to herbicides such as glyphosate, glufosinate or broxynil (Comai et al., Nature 317:741, 1985; Gordon-Kamm et al., Plant Cell 2:603, 1990; Stalker et al., Science 242:419, 1988).

Efficient use of selectable markers is facilitated by a determination of the susceptibility of a plant cell to a particular selectable agent and a determination of the concentration of this agent which effectively kills most, if not all, of the untransformed cells. Some useful concentrations of antibiotics for plant cell transformation include, e.g., 75–100 $\mu$g/ml (kanamycin), 20–50 $\mu$g/ml (hygromycin), or 5–10$\mu$g/ml (bleomycin).

The invention also contemplates DNA constructs in which an expression construct, including a duplicated CsVMV enhancer domain and a promoter, is operably linked to a nucleic acid molecule one wishes to be transcribed. The nucleic acid molecule may have a natural open reading frame (ORF), as well as transcribed 5' and 3' sequences flanking the ORF. Alternatively, it may be in the "antisense" orientation in that it encodes the complement of an RNA molecule or portion thereof. When the construct includes an ORF (which encodes a polypeptide), an enhanced transcription initiation rate is obtained, usually providing an increased amount of the polypeptide. When the construct contains an antisense sequence, complementary to the wild-type molecule, decreases the amount of polypeptide product. In addition, antisense RNA can also function as an inhibitor of replication of RNA (of viral genomes, for example).

Enhanced transcription in plants may find use in enhancing the production of proteins characteristic of the plant (endogenous) or those proteins from other genetic sources (exogenous). For protein production, translational initiation sequences (including a start codon) are included in the constructs, either from the promoter domain, from the attached coding sequences, or from a heterologous source.

Examples of nucleic acid molecules to be expressed under, the control of the expression constructs of the present invention include, without limitation, antisense RNAs (for gene suppression); nutritionally important proteins; growth promoting factors; proteins providing disease resistance; proteins providing protection to the plant under certain environmental conditions (e.g., proteins providing resistance to metal or other toxicity); stress related proteins mediating tolerance to extremes of temperature, freezing, etc.; compounds of medical importance (e.g., anti-microbial; or anti-tumor agents); proteins of specific commercial value; proteins that function as enzymes of metabolic pathways; proteins of structural value to a plant host; and non translatable RNA for the induction of transgene silencing.

For example, an expression construct having a duplicated enhancer domain can be operably linked to a nucleic acid molecule conferring, without limitation, herbicide resistance, fungal disease resistance, bacterial disease resistance, or insect resistance. Similarly, the expression construct can be operably linked to a nucleic acid molecule, the expression of which regulates plant ripening, degradation, color, sweetness, and the like.

The nucleic acid molecules of interest which are transcribed will be of at least about 8 bp, usually at least about 12 bp, more usually at least about 20 bp, and may be about one kb or more in length.

Methods for Making Duplicated Enhancer Domains

A variety of duplicated CsVMV enhancer domains can be produced using standard molecular biology techniques. For example, a duplicated enhancer can be constructed by first mapping restriction enzyme sites in the CsVMV genomic sequence that includes the enhancer domain of interest, then, using the constructed map to determine the appropriate restriction enzymes, excising the domain of interest and recombining it to form a duplicated enhancer domain. Alternatively, a duplicated enhancer domain or an expression construct of the present invention can be synthesized by a variety of methods based on the sequences described herein. Synthesis can be accomplished by chemical synthesis methods for the production of enhancer oligonucleotides. In addition, a nucleic acid molecule can be prepared by the synthesis of a series of oligonucleotides which correspond to different portions of the nucleic acid molecule, and which can be combined by ligation to form larger nucleic acid molecules. Finally, oligonucleotides can be used as primers in a polymerase chain reaction (PCR) to amplify a nucleic acid molecule of interest. The primers can further contain restriction sites to facilitate ligation of the PCR fragments.

The expression constructs are typically prepared employing cloning vectors, where the sequences may be naturally occurring, mutated sequences, synthetic sequences, or combinations thereof The cloning vectors are well known and include prokaryotic or eukaryotic replication systems, markers for selection of transformed host cells, and unique dual restriction sites for insertion or substitution of sequences.

Transgenic Plants

In one embodiment, the invention features a transgenic plant having an expression construct operably linked to a heterologous nucleic acid molecule of interest, the expression of which may cause the plant to have an altered phenotype. Because the promoters of the present invention can function in a wide variety of plants, including both monocot plants and dicot plants, the transgenic plant can be any type of plant that contains an expression construct and that can express the heterologous nucleic acid molecule.

Upon construction of the expression vector, several standard methods are available for introduction of the vector into a plant host, thereby generating a transgenic plant. These methods include: (1) Agrobacterium-mediated transformation (*A. tumefaciens* or *A. rhizogenes*); (2) a particle delivery system; (3) microinjection; (4) polyethylene glycol (PEG) procedures; (5) liposome-mediated DNA uptake; (6) electroporation; (7) chloroplast transformation; and (8) vortexing. The method of transformation is not critical to the invention. Any method which provides for efficient transformation may be employed. As newer methods are available to transform crops or other host cells, they may be directly applied.

One technique of transforming plants with the DNA molecules in accordance with the present invention is by contacting the tissue of such plants with an inoculum of a bacteria transformed with a vector that includes a duplicated CsVMV enhancer domain. Generally, this procedure involves inoculating the plant tissue with a suspension of bacteria and incubating the tissue for 48 to 72 hours on regeneration medium without antibiotics at 25–28° C.

Bacteria from the genus Agrobacterium can be utilized to transform plant cells. Suitable species of such bacterium include *Agrobacterium tumefaciens* and *Agrobacterium rhizogenes*. *Agrobacterium tumefaciens* (e.g., strains C58, LBA4404, or EHA105) is particularly useful due to its well-known ability to transform plants.

Another approach to transforming plant cells with a gene which imparts resistance to pathogens is particle bombardment (also known as biolistic transformation) of the,host cell. This can be accomplished in one of several ways, such as those disclosed in U.S. Pat. Nos. 4,945,050, 5,036,006, and 5,100,792, all to Sanford et al., and in Emerschad et al., Plant Cell Reports, 14:6–12, 1995.

Once plant tissue is transformed in accordance with the present invention, it is regenerated to form a transgenic plant. Generally, regeneration is accomplished by culturing transformed tissue on medium containing the appropriate growth regulators and nutrients to allow for the initiation of shoot meristems. Appropriate selection agents are added to the regeneration medium to select for the development of transformed cells. Following shoot initiation, shoots are allowed to develop in tissue culture and may be screened for marker gene activity.

In general, transfer and expression of transgenes in plant cells are now routine practices to those skilled in the art, and have become major tools to carry out gene expression studies in plants and to produce improved plant varieties of agricultural or commercial interest.

EXAMPLE 1

Preparation of Duplicated CsVMV Enhancer Domains

Duplicated CsVMV enhancer domains were produced by internal splicing and addition. The preparation of six duplicated CsVMV enhancer domains is outlined below.

The starting plasmid was pBluscript-CsVMV, which contained CsVMV promoter fragment extending from position −443 to +72, (nucleotides 1 to 515 of SEQ ID NO: 1). Due to the absence of convenient restriction sites in the CsVMV promoter fragment, polymerase chain reaction (PCR) was used to generate a set of terminal and internal fragments.

EXAMPLE 2

Construction of Plant Expression Vectors

The pGEN plant expression vector with appropriate multiple cloning sites was used to introduce the duplicated CsVMV enhancer domains into tobacco plants. The different duplicated enhancer domains generated in Example 1 were cloned into two versions of the pGEN vectors using standard techniques.

EXAMPLE 3

Development of Transgenic Plants

The pGEN derived plasmids carrying a non-duplicated CsVMV enhancer domain, a duplicated CsVMV enhancer domain and a promoterless construct were transformed separately into *Agrobacterium tumefaciens* strain GV3850. *Agrobacterium tumefaciens*-mediated transformations of *Nicotiana tabacum* cv KY14 were performed as previously described (Horsch et al., Plant Molecular Biology Manual). Approximately 40 kanamycin resistant transgenic lines were generated for each construct. The plants were grown to maturity in a greenhouse.

EXAMPLE 4

Expression Analysis of CsVMV Expression Constructs

Histochemical Analysis of Expression in Calli and Young Plants

Figure 5:
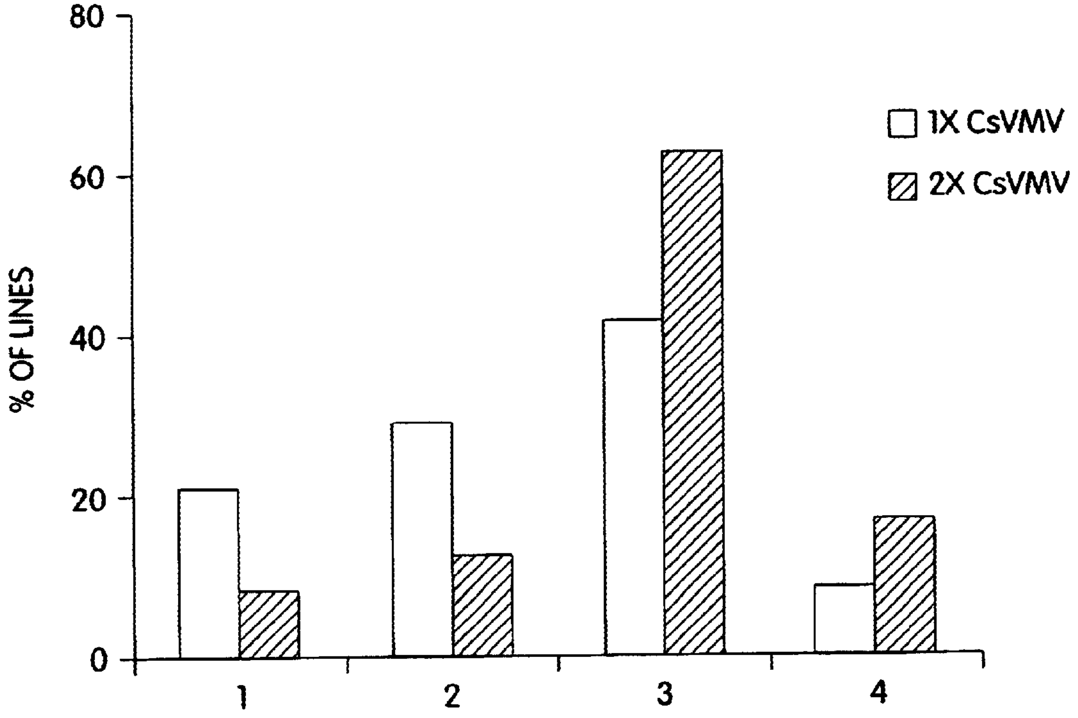
FIG. 5 is a schematic, illustration showing the frequency of GUS staining in transgenic lines expressing GUS from expression constructs containing either an unduplicated CsVMV enhancer domain (1×CsVMV) or a duplicated CsVMV enhancer domain (CV-2; 2×CsVMV).

Histochemical GUS analyses of plasmid-transformed calli and plantlets were carried out to analyze the expression levels of expression constructs containing the unduplicated ("1×") CsVMV enhancer and the duplicated ("2×") CsVMV enhancer (corresponding to expression construct CV-2; see FIGS. 2A and 4A). Calli and the top two leaves of plantlets from each independent transformant were collected for GUS stain analysis. Fresh tissues were taken and incubated for three hours, six hours, and overnight at 37° C. in 2 ml reaction buffer containing 1 mM 5-bromo-4-chloro-3-indolyl glucuronide (x-gluc), 100 mM sodium phosphate buffer pH 7.2, potassium ferrocyanide, potassium ferricyanide, and 0.2% Triton x-100. GUS staining was scored using a scale of 1 to 4 from light staining to heavy staining, as shown in FIG. 5. Scoring was as follows: Score 4—all tissue stained blue and solution was also blue 3—most tissue stained dark blue; 2—some tissue stained light blue; 1—tissue had light blue spots; 0—no staining.

The promterless plants and calli were all scored 0. In contrast, none of the transgenic plants were scored 0. This indicated that 100% of plants contained and expressed the GUS reporter gene. The transgenic plants started to show the blue color after 30 minutes in the stain solution. Most plants stained blue after three hours in the solution. A higher percentage of plants containing the double promoter showed high rating scores (80% of plants for CV-2 were rated 3 or 4, compared with 49% for 1×construct). In some high lines containing the CV-2 expression construct, expression appeared about one hour before expression in plants containing 1×expression constructs. These data thus indicated that the CV-2 expression construct generates transgenic plants with higher expression when compared with the 1×CsVMV enhancer.

Glucuronidase Assays for the Transgenic Lines Containing 1× and 2×CsVMV promoters.

Figure 6:
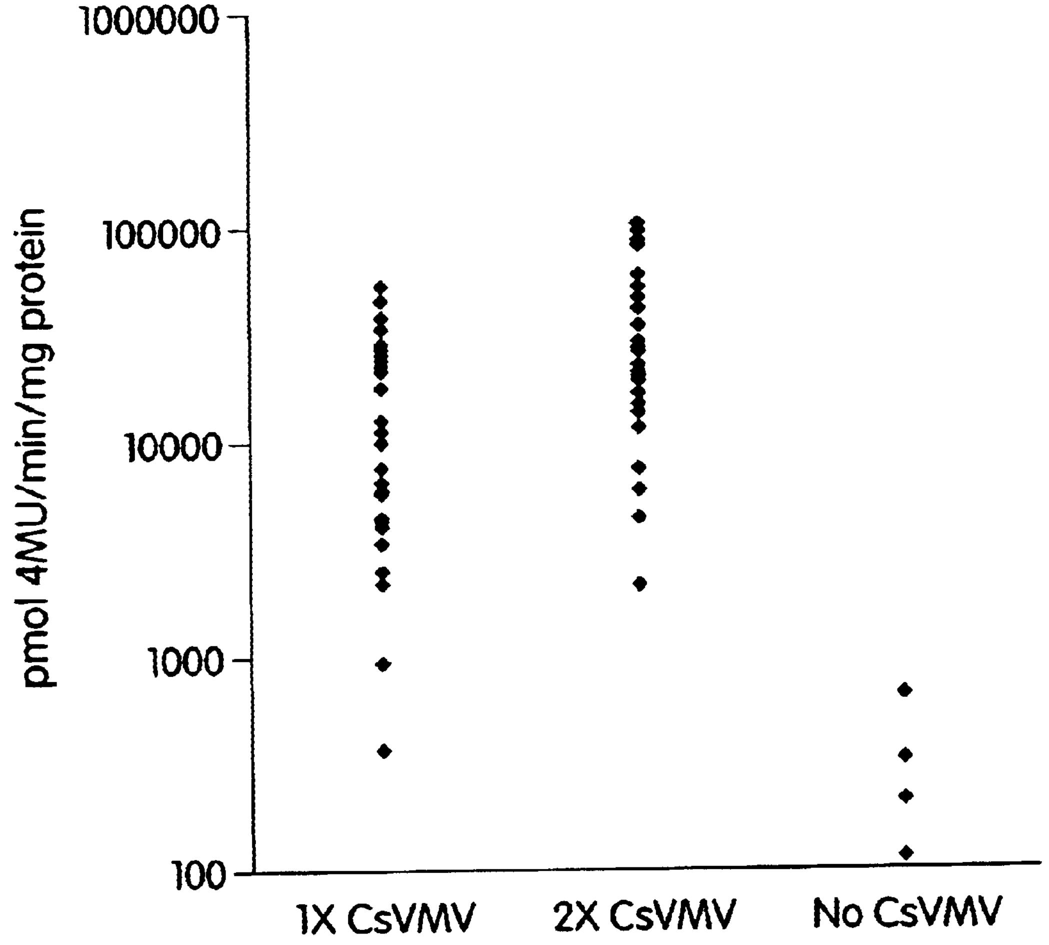
FIG. 6 is a schematic illustration showing GUS activity in transgenic lines expressing GUS from expression constructs containing unduplicated CsVMV enhancer domains ("1× CsVMV") or duplicated CsVMV enhancer domains (construct CV-2; "2×CsVMV").
Figure 7:
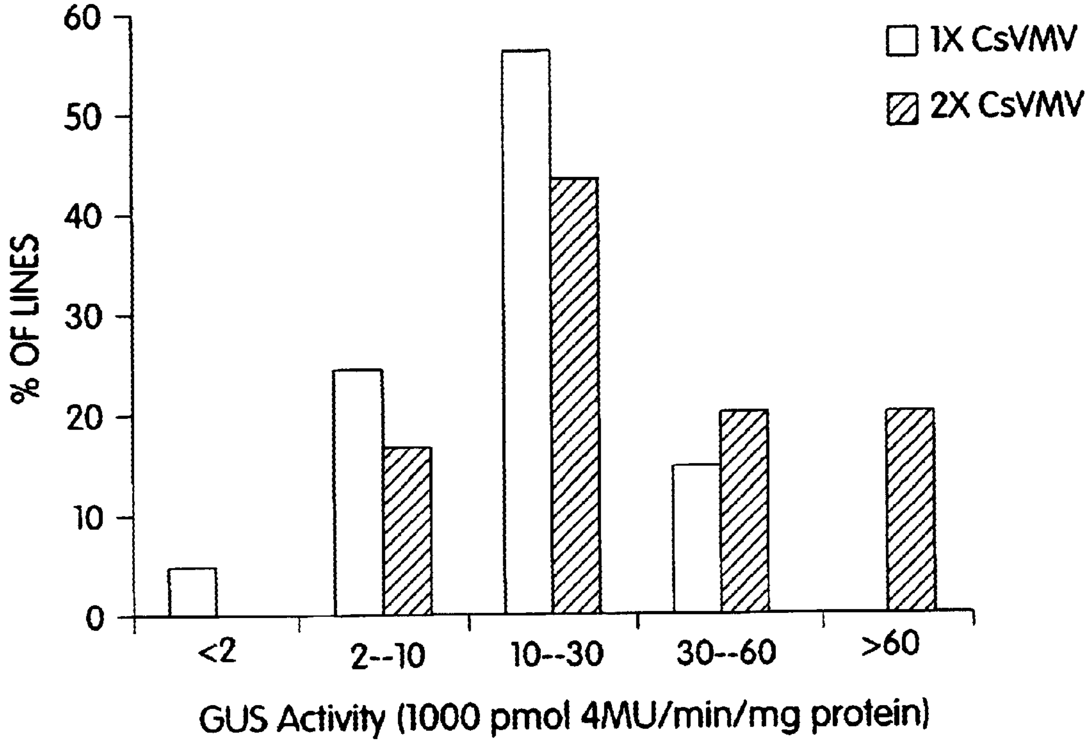
FIG. 7 is a schematic illustration showing the frequency of GUS staining in transgenic lines expressing GUS from expression constructs containing either 1×CsVMV or 2×CsVMV.

GUS activities in protein extracts prepared from leaf tissues were quantitatively measured using a fluorometric assay (Jefferson et al., EMBO J. 6:3901–7, 1087). The samples were collected from interveinal tissues of young leaves from transgenic plants generated in Example 3. Forty-one samples, 30 samples and 4 samples from independent transgenic lines were assayed for an unduplicated enhancer construct, a duplicated enhancer construct, and a promoterless construct, respectively. FIG. 6 depicts values of GUS activities for different constructs. The variation among lines containing the same expression construct can be attributed to a combination of factors including a putative position effect reflecting the influence of the surrounding chromatin, on gene expression, differences in copy number, and gene silencing. The data confirmed the histochemical localization data for GUS expression in transgeric plants. The range of the GUS expression was 374 to 54337 pmol 4MU/mom/mg protein for the 1×CsVMV construct (mean=19596) and 2152 to 106799 for the 2×CsVMV construct (mean=35678). The average value for these transgenic plants was 331 for promoterless plants. FIG. 7 showed the frequency of transgenic lines exhibited different level of GUS activities. None of the plants from 2×CsVMV had GUS activities lower than2000 pmol 4 MU/min/mg protein. We confirmed the foregoing results by GUS staining the top two leaves from the same transgenic plants.

Other Embodiments

All publications mentioned in this specification are herein incorporated by reference to the same extent as if each independent publication was specifically and individually indicated to be incorporated by reference.

While the invention has been described in connection with specific embodiments thereof, it will be understood that it is capable of further modifications. This application is intended to cover any variations, uses, or adaptations following, in general, the principles of the invention and including such departures from the present disclosure within known or customary practice within the art to which the invention pertains and may be applied to the essential features hereinbefore set forth.

What is claimed is:

1. An expression construct comprising SEQ ID NO:2, SEQ ID NO:3, SEQ ID NO:4, SEQ ID NO:5, or SEQ ID NO:6.

2. The expression construct of claim 1, wherein said expression construct is operably linked to a nucleic acid molecule of interest.

3. The construct of claim 2, wherein said nucleic acid molecule of interest encodes a protein, a protein providing disease or insect resistance, an RNA, an antisense RNA, a nontranslatable RNA, an RNA that induces transgene silencing, or a selectable marker.

4. An expression construct as in any one of claim 1, 2, or 3, in which the expression construct comprises SEQ ID NO:2.

5. An expression construct as in any one of claim 1, 2, or 3, in which the expression construct comprises SEQ ID NO:3.

6. An expression construct as in any one of claim 1, 2, or 3, in which the expression construct comprises SEQ ID NO:4.

7. An expression construct as in any one of claim 1, 2, or 3, in which the expression construct comprises SEQ ID NO:5.

8. An expression construct as many one of claim 1, 2, or 3, in which the expression construct comprises SEQ ID NO:6.

9. An isolated nucleic acid molecule comprising SEQ ID NO:2, SEQ ID NO:3, SEQ ID NO:4, SEQ ID NO:5, or SEQ ID NO:6.

10. The nucleic acid molecule of claim 9, wherein said nucleic acid molecule is operably linked to a nucleic acid molecule of interest.

11. The nucleic acid molecule of claim 10, wherein said nucleic acid molecule of interest encodes a protein, a protein providing disease or insect resistance, an RNA, an antisense RNA, a nontranslatable RNA, an RNA that induces transgene silencing, or a selectable marker.

12. An isolated nucleic acid molecule as in any one of claim 9, 10, or 11, in which the nucleic acid molecule comprises SEQ ID NO:2.

13. An isolated nucleic acid molecule as in any one of claim 9, 10, or 11, in which the nucleic acid molecule comprises SEQ ID NO:3.

14. An isolated nucleic acid molecule as in any one of claim 9, 10, or 11, in which the nucleic acid molecule comprises SEQ ID NO:4.

15. An isolated nucleic molecule as in any one of claim 9, 10, or 11, in which the nucleic acid molecule comprises SEQ ID NO:5.

16. An isolated nucleic acid molecule as in any one of claim 9, 10, or 11, in which the nucleic acid molecule comprises SEQ ID NO:6.

17. A cell comprising an expression construct comprising SEQ ID NO:2, SEQ ID NO:3, SEQ ID NO:4, SEQ ID NO:5, or SEQ ID NO:6.

18. The cell of claim 17, said expression construct is operably linked to a nucleic acid molecule of interest.

19. The cell of claim 18, wherein said nucleic acid molecule of interest encodes a protein, a protein providing disease or insect resistance, an RNA, an antisense RNA, a nontranslatable RNA, an RNA that induces transgene silencing, or a selectable marker.

20. A cell as in any one of claim 17, 18, or 19, in which the expression construct comprises SEQ ID NO:2.

21. A cell as in any one of claim 17, 18, or 19, in which the expression construct comprises SEQ ID NO:3.

22. A cell as in any one of claim 17, 18, or 19, in which the expression construct comprises SEQ ID NO:4.

23. A cell as in any one of claim 17, 18, or 19, in which the expression construct comprises SEQ ID NO:5.

24. A cell as in any one of claim 17, 18, or 19, in which the expression construct comprises SEQ ID NO:6.

25. A plant comprising an expression construct comprising SEQ ID NO:2, SEQ ID NO:3, SEQ ID NO:4, SEQ ID NO:5, or SEQ ID NO:6.

26. The plant of claim 25, wherein said expression construct is operably linked to a nucleic acid molecule of interest.

27. The plant of claim 26, wherein said nucleic acid molecule of interest encodes a protein, a protein providing disease or insect resistance, an RNA, an antisense RNA, a nontranslatable RNA, an RNA that induces transgene silencing, or a selectable marker.

28. A plant as in any one of claim 25, 26, or 27, in which the expression construct comprises SEQ ID NO:2.

29. A plant as in any one of claim 25, 26, or 27, in which the expression construct comprises SEQ ID NO:3.

30. A plant as in any one of claim 25, 26, or 27, in which the expression construct comprises SEQ ID NO:4.

31. A plant as in any one of claim 25, 26, or 27, in which the expression construct comprises SEQ ID NO:5.

32. A plant as in any one of claim 25, 26, or 27, in which the expression construct comprises SEQ ID NO:6.

* * * * *

UNITED STATES PATENT AND TRADEMARK OFFICE
CERTIFICATE OF CORRECTION

PATENT NO. : 6,664,384 B1
DATED : December 16, 2003
INVENTOR(S) : Dongmei Xu and Mark T. Nielsen It is certified that error appears in the above-identified patent and that said Letters Patent is hereby corrected as shown below:

Title page,
Item [73], Assignee, replace "Profigen" with -- ProfiGen --.
Item [56], References Cited, U.S. PATENT DOCUMENTS, insert the following:

| | | | | | |
|---|---|---|---|---|---|
| -- | 5,164,316 | 11/17/92 | McPherson et al. | 435 | |
| | 5,196,525 | 3/23/93 | McPherson et al. | 536 | |
| | 5,322,938 | 6/21/94 | McPherson et al. | 536 | |
| | 5,352,605 | 10/4/94 | Fraley et al. | 435 | |
| | 5,359,142 | 10/25/94 | McPherson et al. | 800 | |
| | 5,424,200 | 6/13/95 | McPherson et al. | 435 | --. |

OTHER PUBLICATIONS, insert the following:

--Gardner, "Plant viral vectors: CaMV as an experimental tool", Genetic Engineering of Plants, and Agricultural Perspective, Proceedings of a Symposium held August 15-19, 1982 at the University of California, Davis, California, Kusuge et al. Ed., pp. 124-125.

Guilley et al., "Transcription of cauliflower mosaic virus DNA: Detection of promoter sequences, and characterization of transcripts" *Cell* 30:763-773 (1992).

Hohn et al., "Cauliflower mosaic virus on its way to becoming a useful plant vector" *Current Topics in Microbiology and Immunology* 96:194-236 (1982).

Howell et al., "Cloned Cauliflower mosaic virus DNA infects turnips (*Brassica rapa*)" *Science* 208:1265-1267 (1980).--.

--McNight et al., "Isolation and mapping of small cauliflower mosaic virus DNA fragments active as promoters in *Escherichia coli*" *Journal of Virology* 37:673-682 (1981).

Verdaguer et al., "Isolation and expression in transgenic tobacco and rice plants, of the cassava vein mosaic virus (CVMV) promoter" *Plant Molecular Biology* 21:1129-1139 (1996).--.

Column 3,
Line 21, replace "transgeinic" with -- transgenic --; and
Line 30, replace "in, the" with -- in the --.

Column 4,
Line 51, replace "d6mains" with -- domains --.

UNITED STATES PATENT AND TRADEMARK OFFICE

CERTIFICATE OF CORRECTION

PATENT NO. : 6,664,384 B1
DATED : December 16, 2003
INVENTOR(S) : Dongmei Xu and Mark T. Nielsen It is certified that error appears in the above-identified patent and that said Letters Patent is hereby corrected as shown below:

Column 7,
Line 1, replace "(GUS);," with -- (GUS); --;
Line 5, replace "1996).," with -- 1996). --;
Line 47, replace "under, the" with -- under the --; and
Line 55, replace "anti-microbial;" with -- anti-microbial --.

Column 9,
Line 9, replace "the,host" with -- the host --; and
Line 37, replace "pBluscript-CsVMV" with -- pBluescript-CsVMV --.

Column 10,
Line 59, replace "4MU/mom/mg" with -- 4MU/min/mg --; and
Line 65, replace "than2000" with -- than 2000 --.

Signed and Sealed this

Tenth Day of May, 2005

JON W. DUDAS
*Director of the United States Patent and Trademark Office*

SEQUENCE LISTING

```
<160> NUMBER OF SEQ ID NOS:  6

<210> SEQ ID NO 1
<211> LENGTH: 515
<212> TYPE: DNA
<213> ORGANISM: cassava vein mosaic virus

<400> SEQUENCE: 1

ccagaaggta attatccaag atgtagcatc aagaatccaa tgtttacggg aaaaactatg     60

gaagtattat gtgagctcag caagaagcag atcaatatgc ggcacatatg caacctatgt    120

tcaaaaatga agaatgtaca gatacaagat cctatactgc cagaatacga agaagaatac    180

gtagaaattg aaaaagaaga accaggcgaa gaaaagaatc ttgaagacgt aagcactgac    240

gacaacaatg aaaagaagaa gataaggtcg gtgattgtga aagagacata gaggacacat    300

gtaaggtgga aaatgtaagg gcggaaagta accttatcac aaaggaatct tatcccccac    360

tacttatcct tttatatttt tccgtgtcat ttttgccctt gagttttcct atataaggaa    420

ccaagttcgg catttgtgaa aacaagaaaa aatttggtgt aagctatttt ctttgaagta    480

ctgaggatac aagttcagag aaatttgtaa gtttg                               515


<210> SEQ ID NO 2
<211> LENGTH: 853
<212> TYPE: DNA
<213> ORGANISM: Artificial Sequence
<220> FEATURE:
<223> OTHER INFORMATION: based on cassava vein mosaic virus

<400> SEQUENCE: 2

ccagaaggta attatccaag atgtagcatc aagaatccaa tgtttacggg aaaaactatg     60

gaagtattat gtgagctcag caagaagcag atcaatatgc ggcacatatg caacctatgt    120

tcaaaaatga agaatgtaca gatacaagat cctatactgc cagaatacga agaagaatac    180

gtagaaattg aaaaagaaga accaggcgaa gaaaagaatc ttgaagacgt aagcactgac    240

gacaacaatg aaaagaagaa gataaggtcg gtgattgtga aagagacata gaggacacat    300

gtaaggtgga aaatgtaagg gcggaaagta acaagcttcc agaaggtaat tatccaagat    360

gtagcatcaa gaatccaatg tttacgggaa aaactatgga agtattatgt gagctcagca    420

agaagcagat caatatgcgg cacatatgca acctatgttc aaaaatgaag aatgtacaga    480

tacaagatcc tatactgcca gaatacgaag aagaatacgt agaaattgaa aaagaagaac    540

caggcgaaga aaagaatctt gaagacgtaa gcactgacga caacaatgaa aagaagaaga    600

taaggtcggt gattgtgaaa gagacataga ggacacatgt aaggtggaaa atgtaagggc    660

ggaaagtaac cttatcacaa aggaatctta tcccccacta cttatccttt tatatttttc    720

cgtgtcattt ttgcccttga gttttcctat ataaggaacc aagttcggca tttgtgaaaa    780

caagaaaaaa tttggtgtaa gctattttct ttgaagtact gaggatacaa gttcagagaa    840
```

-continued

```
atttgtaagt ttg                                                     853

<210> SEQ ID NO 3
<211> LENGTH: 593
<212> TYPE: DNA
<213> ORGANISM: Artificial Sequence
<220> FEATURE:
<223> OTHER INFORMATION: based on cassava vein mosaic virus

<400> SEQUENCE: 3

ccagaaggta attatccaag atgtagcatc aagaatccaa tgtttacggg aaaaactatg    60

gaagtattat gtgagctcag caagaagcag atcaatatgc ggcacatatg caacctatgt   120

tcaaaaatga agaatgtaca gatacaagat cctatactgc cagaatacga agaagaatac   180

gtagaaattg aaaaagaaga accaggcgaa gaaaagaatc ttgaagacgt aagcactgac   240

gacaacaatg aaaagaagaa gataaggtcg gtgattgtga aagagacata gaggacacat   300

gtaaggtgga aaatgtaagg gcggaaagta acaagcttga taaggtcggt gattgtgaaa   360

gagacataga ggacacatgt aaggtggaaa atgtaagggc ggaaagtaac cttatcacaa   420

aggaatctta tcccccacta cttatccttt tatatttttc cgtgtcattt ttgcccttga   480

gttttcctat ataaggaacc aagttcggca tttgtgaaaa caagaaaaaa tttggtgtaa   540

gctattttct ttgaagtact gaggatacaa cttcagagaa atttgtaagt ttg          593

<210> SEQ ID NO 4
<211> LENGTH: 857
<212> TYPE: DNA
<213> ORGANISM: Artificial Sequence
<220> FEATURE:
<223> OTHER INFORMATION: based on cassava vein mosaic virus

<400> SEQUENCE: 4

ccagaaggta attatccaag atgtagcatc aagaatccaa tgtttacggg aaaaactatg    60

gaagtattat gtgagctcag caagaagcag atcaatatgc ggcacatatg caacctatgt   120

tcaaaaatga agaatgtaca gatacaagat cctatactgc cagaatacga agaagaatac   180

gtagaaattg aaaaagaaga accaggcgaa gaaaagaatc ttgaagacgt aagcactgac   240

gacaacaatg aaaagaagaa gcttccagaa ggtaattatc caagatgtag catcaagaat   300

ccaatgttta cgggaaaaac tatggaagta ttatgtgagc tcagcaagaa gcagatcaat   360

atgcggcaca tatgcaacct atgttcaaaa atgaagaatg tacagataca agatcctata   420

ctgccagaat acgaagaaga atacgtagaa attgaaaaag aagaaccagg cgaagaaaag   480

aatcttgaag acgtaagcac tgacgacaac aatgaaaaga agaagataag gtcggtgatt   540

gtgaaagaga catagaggac acatgtaagg tggaaaatgt aagggcggaa agtaacaagc   600

ttgataaggt cggtgattgt gaaagagaca tagaggacac atgtaaggtg gaaaatgtaa   660

gggcggaaag taaccttatc acaaaggaat cttatccccc actacttatc cttttatatt   720

tttccgtgtc atttttgccc ttgagttttc ctatataagg aaccaagttc ggcatttgtg   780

aaaacaagaa aaaatttggt gtaagctatt ttctttgaag tactgaggat acaacttcag   840

agaaatttgt aagtttg                                                  857

<210> SEQ ID NO 5
<211> LENGTH: 931
<212> TYPE: DNA
<213> ORGANISM: Artificial Sequence
<220> FEATURE:
<223> OTHER INFORMATION: based on cassava vein mosaic virus
```

-continued

<400> SEQUENCE: 5

```
ccagaaggta attatccaag atgtagcatc aagaatccaa tgtttacggg aaaaactatg      60
gaagtattat gtgagctcag caagaagcag atcaatatgc ggcacatatg caacctatgt     120
tcaaaaatga agaatgtaca gatacaagat cctatactgc cagaatacga agaagaatac     180
gtagaaattg aaaaagaaga accaggcgaa gaaaagaatc ttgaagacgt aagcactgac     240
gacaacaatg aaaagaagaa gataaggtcg gtgattgtga aagagacata gaggacacat     300
gtaaggtgga aaatgtaagg gcggaaagta acaagcttcc agaaggtaat tatccaagat     360
gtagcatcaa gaatccaatg tttacgggaa aaactatgga agtattatgt gagctcagca     420
agaagcagat caatatgcgg cacatatgca acctatgttc aaaaatgaag aatgtacaga     480
tacaagatcc tatactgcca gaatacgaag aagaatacgt agaaattgaa aaagaagaac     540
caggcgaaga aaagaatctt gaagacgtaa gcactgacga caacaatgaa aagaagaaga     600
taaggtcggt gattgtgaaa gagacataga ggacacatgt aaggtggaaa atgtaagggc     660
ggaaagtaac aagcttgata aggtcggtga ttgtgaaaga gacatagagg acacatgtaa     720
ggtggaaaat gtaagggcgg aaagtaacct tatcacaaag gaatcttatc cccactact      780
tatcctttta tatttttccg tgtcattttt gcccttgagt tttcctatat aaggaaccaa     840
gttcggcatt tgtgaaaaca agaaaaaatt tggtgtaagc tattttcttt gaagtactga     900
ggatacaact tcagagaaat ttgtaagttt g                                    931
```

<210> SEQ ID NO 6
<211> LENGTH: 931
<212> TYPE: DNA
<213> ORGANISM: Artificial Sequence
<220> FEATURE:
<223> OTHER INFORMATION: based on cassava vein mosaic virus

<400> SEQUENCE: 6

```
ccagaaggta attatccaag atgtagcatc aagaatccaa tgtttacggg aaaaactatg      60
gaagtattat gtgagctcag caagaagcag atcaatatgc ggcacatatg caacctatgt     120
tcaaaaatga agaatgtaca gatacaagat cctatactgc cagaatacga agaagaatac     180
gtagaaattg aaaaagaaga accaggcgaa gaaaagaatc ttgaagacgt aagcactgac     240
gacaacaatg aaaagaagaa gataaggtcg gtgattgtga aagagacata gaggacacat     300
gtaaggtgga aaatgtaagg gcggaaagta acaagcttgt tactttccgc ccttacattt     360
tccaccttac atgtgtcctc tatgtctctt tcacaatcac cgaccttatc ttcttctttt     420
cattgttgtc gtcagtgctt acgtcttcaa gattcttttc ttcgcctggt tcttcttttt     480
caatttctac gtattcttct tcgtattctg gcagtatagg atcttgtatc tgtacattct     540
tcatttttga acataggttg catatgtgcc gcatattgat ctgcttcttg ctgagctcac     600
ataatacttc catagttttt cccgtaaaca ttggattctt gatgctacat cttggataat     660
taccttctgg aagcttgata aggtcggtga ttgtgaaaga gacatagagg acacatgtaa     720
ggtggaaaat gtaagggcgg aaagtaacct tatcacaaag gaatcttatc cccactact      780
tatcctttta tatttttccg tgtcattttt gcccttgagt tttcctatat aaggaaccaa     840
gttcggcatt tgtgaaaaca agaaaaaatt tggtgtaagc tattttcttt gaagtactga     900
ggatacaact tcagagaaat ttgtaagttt g                                    931
```